United States Patent
Siegenthaler

(10) Patent No.: US 6,620,790 B2
(45) Date of Patent: Sep. 16, 2003

(54) ISOLATED ARACHIDONIC ACID-BINDING HETEROMER AND ITS USE IN COSMETICS AND PHARMACEUTICS

(75) Inventor: Georges Siegenthaler, Belevue (CH)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/214,272

(22) PCT Filed: Jun. 30, 1997

(86) PCT No.: PCT/FR97/01164

§ 371 (c)(1),
(2), (4) Date: Apr. 9, 1999

(87) PCT Pub. No.: WO98/00095

PCT Pub. Date: Jan. 8, 1998

(65) Prior Publication Data

US 2001/0007674 A1 Jul. 12, 2001

(30) Foreign Application Priority Data

Jul. 2, 1909 (FR) .............................. 96 08219

(51) Int. Cl.[7] .............................................. A61K 38/16
(52) U.S. Cl. ................................ 514/21; 514/2; 514/12; 530/350; 424/401
(58) Field of Search .................. 435/240.27; 530/378.9, 530/350; 514/12, 2, 21; 424/401

(56) References Cited

U.S. PATENT DOCUMENTS 5,350,687 A * 9/1994 Odink et al. ............. 530/388.1

FOREIGN PATENT DOCUMENTS

| EP | 0 585 201 A1 | * | 3/1994 |
| EP | 0 585 201 | | 3/1994 |
| WO | WO 98/00095 | * | 1/1998 |

OTHER PUBLICATIONS

Edgeworth et al., *"Ionomycin–Regulated Phosphorylation of the Myeloid Calcium–Binding Protein P14"*, Nature, vol. 342, pp. 189–192 (Nov. 1989), Nature Publishing Group, Great Britain.

Edgeworth et al., *"Identification of P8, 14 as a Highly Abundant Heterodimeric Calcium Binding Protein Complex of Myeloid Cells"*, Journal of Biological Chemistry, vol. 266, No. 12, pp. 7706–7713 (Apr. 1991), The American Society for Biochemistry and Molecular Biology, Bethesda, Maryland, USA.

Teigelkamp et al., *"Calcium–Dependent Complex Assembly of the Myeloid Differentiation Proteins MRP–8 and MRP–14"*, Journal of Biological Chemistry, vol. 266, No. 20, pp. 13462–13467 (Jul. 1991) The American Society for Biochemistry and Molecular Biology, Bethesda, Maryland, USA.

Roth et al., *"MRP8 and MRP 14, S–100–Like Proteins Associated with Myeloid Differentation, are Translocated to Plasma Membrane and Intermediate Filaments in a Calcium–Dependent Manner"*, Blood, vol. 82, No. 6, pp. 1875–1883 (Sep. 1993), American Society of Hematology, Washington, D.C., USA.

Goebeler et al., *"Increase of Calcium Levels in Epithelial Cells Induces Translocation of Calcium–Binding Proteins Migration Inhibitory Factor–Related Protein 8 (MPR8) and MRP14 to Keratin Intermediate Filaments"*, Biochemical Journal, vol. 309, pp. 419–424 (Jul. 1995), Portland Press Limited, London, Great Britain.

Guignard et al., *"Phosphorylation of Myeloid–Related Proteins MRP–14 and MRP–8 During Human Neutrophil Activation"*, European Journal of Biochemistry, vol. 241, pp. 265–271 (Oct. 1996), Blackwell Science on behalf of the Federation of European Biochemical Societies, Oxford, Great Britain.

Hagens et al., *Frontiers in Bioactive Lipids*, ed. Jack Y. Vanderhoek, pp. 61–66, (1996), Plenum Press, New York, New York, USA.

Siegenthaler et al., *"Myeloid–Related Protein (MRP) 8 and MRP14, Calcium–Binding Proteins of the S100 Family, are Secreted by Activated Monocytes via a Novel. Tubulin–Dependedt Pathway"*, Journal of Biological Chemistry, vol. 272, pp. 9371–9377 (Apr. 1997), The American Society for Biochemistry and Molecular Biology, Bethesda, Maryland, USA.

Roulin et al., *"The Fatty Acid–Binding Heterocomplex FA–p34 Formed by S100A8 and S100A9 is the Major Fatty Acid Carrier in Neutorphilis and Translocates from the Cytosol to the Membrane upon Stimulation"*, Experimental Cell Research, vol. 247, pp. 410–421 (1999), Harcourt, Inc. a member of the Reed Elsevier Group, New York, New York, USA.

Hagens et al., *"S100 Proteins and Fatty Acid Transport are Altered in Skin Diseases"*, Calcium: The Molecular Basis of Calcium Action in Biology and Medicine, R. Pochet et al. (Editors), pp. 477–492, (2000), Kluwer Academic Publishers, The Netherlands.

Siegenthaler et al., *"Purification and Characterization of the Human Epidermal Fatty Acid–Binding Protein: Localization During Epidermal Cell Differentiation In Vivo and In Vitro"*, Biochem. J., (1994) 302, 363–371, Portland Press, Great Britain.

(List continued on next page.)

Primary Examiner—Christopher S. F. Low
Assistant Examiner—David Lukton
(74) Attorney, Agent, or Firm—Burns, Doane, Swecker & Mathis, L.L.P.

(57) ABSTRACT

The invention discloses an isolated arachidonic acid-binding heteromer that can be used in particular to stimulate and/or induce hair growth and/or check hair loss or to accelerate the healing process or to test substances affecting the activity of fatty acids or further as a diagnostic tool.

19 Claims, No Drawings

OTHER PUBLICATIONS

Glatz et al., "*Cytoplasmic Fatty Acid Binding Protein: Significance for Intracellular Transport of Fatty Acids and Putative Role on Signal Transduction Pathways*", Prostaglandins Leukotrienes and Essential Fatty Acids, (1993), Longman Group, UK Ltd., Great Britain.

K. Odink: "Two calcium–binding proteins in infiltrate macrophages of rheumatoid arthritis", Nature, vol. 330, No. 6143, 1987, pp. 80–82, XP000645407.

G. Siegenthaler: "Purification and characterization of the human epidermal fatty acid–binding protein: localization during epidermal cell diferentiation in vivo and in vitro", Biochem, J., vol. 302, No. Part 2, 1994, pp. 363–371, XP000645424.

P. Madsen: "Molecular cloning and expression of novel keratinocyte protein (psoriasis–associated fatty acid–binding protein [PA–FABP]) that is highly up–regulated in psoriatic skin and that shares similarity to fatty acid–binding proteins", J. Invest. Dermatol., vol. 99, No. 3, 1992, pp. 299–305, XP000645498.

C.D. Kane: "Expression, purification, and ligand–binding analysis of recombinant keratinocyte lipid–binding protein (MAL–1), an intracellular lipid–binding protein found overexpressed in neoplastic skin cells", Biochemistry, vol. 35, No. 9, Mar. 1996, pp. 2894–2900, XP000645405.

Edgeworth et al, *Nature*, vol. 342, pp. 189–192 (Nov. 1989).

Edgeworth et al, *Journal of Biological Chemistry*, vol. 266, No. 12, pp. 7706–7713 (Apr. 1991).

Teigelkamp et al, *Journal of Biological Chemistry*, vol. 266, No. 20, pp. 13462–13467 (Jul. 1991).

Hessian et al, *Journal of Leukocyte Biology*, vol. 53, pp. 197–204 (Feb. 1993).

Roth et al, *Blood*, vol. 82, No. 6, pp. 1875–1883 (Sep. 1993).

Goebeler et al, *Biochemical Journal*, vol. 309, pp. 419–424 (Jul. 1995).

Guignard et al, *European Journal of Biochemistry*, vol. 241, pp. 265–271 (Oct. 1996).

Hagens et al, in *Frontiers in Bioactive Lipids*, ed. Jack Y. Vanderhoek, Plenum Press, New York, pp. 61–66 (1996).

Siegenthaler et al, *Journal of Biological Chemistry*, vol. 272, pp. 9371–9377 (Apr. 1997).

Rammes et al, *Journal of Biological Chemistry*, vol. 272, pp. 9496–9502 (Apr. 1997).

Klempt et al, *FEBS Letters*, vol. 408, pp. 81–84 (May 1997).

Roulin et al, *Experimental Cell Research*, vol. 247, pp. 410–421 (1999).

Hessian et al., "*MRP–8 and MRP–14*, Two Abundant $Ca^{2+}$–Binding Proteins of Neutrophils and Monocytes", Journal of Leukocyte Biology, vol. 53, pp. 197–204 (Feb. 1993), Society for Leukocyte Biology, Bethesda, Maryland USA.

Rammes et al., *Journal of Biological Chemistry*, vol. 272, pp. 9496–9502 (Apr. 1997), The American Society for Biochemistry and Molecular Biology, Bethesda, Maryland, USA.

Klempt et al., "The Heterodimer of the $Ca^{2+}$–Binding Proteins MRP8 and MRP14 Binds Arachidonic Acid", *FEBS Letters*, vol. 408, pp. 81–84 (May 1997), Elsevier Science, Oxford, Great Britain.

\* cited by examiner

ISOLATED ARACHIDONIC ACID-BINDING HETEROMER AND ITS USE IN COSMETICS AND PHARMACEUTICS

This application is a national stage filing under 35 U.S.C. §371 of International Patent Application No. PCT/FR97/01164, filed Jun. 30, 1997 and designating the United States, which International Application was published by the International Bureau on Jan. 8, 1998 in French, not in English, as WO 98/00095.

1. Field of the Invention

The invention relates to an isolated arachidonic heteromer. This heteromer can be used in particular to stimulate and/or induce hair growth and/or check hair loss or to accelerate the healing process or to test substances that affect the activity of fatty acids or further as a diagnostic tool.

2. Description of the Related Art

Fatty acids, such as arachidonic acid and its derivatives, play an important role in particular in the synthesis of cell or nuclear membranes, in the inflammation mechanism as precursors to mediators and as skin barriers, as well as in the control of skin cell differentiation and proliferation.

Furthermore, it is written that fatty acids affect the expression of many genes through nuclear receptors, called PPARs (peroxisome proliferator-activated nuclear receptors).

Due to their hydrophobic and brittle characteristics, fatty acids are disintegrated, stabilized and carried in the biological environment by specific cytosolic carrier proteins of low molecular weight (15 kDa) called FABP (fatty acid-binding proteins). The skin it the most active tissue as far as the synthesis of lipids is concerned. But, certain lipids called essential fatty acids, such as arachidonic acid and linoleic acid, cannot be synthesized by these cells and must therefore be acquired from humors, The capture and release mechanism of these fatty acids by the cells, and more specifically by the keratinocytes, is not known, However, it seems that this mechanism takes place by means of carrier proteins, even though to date the identification of these proteins remains unsuccessful. Recently, among the keratinocytes, a specific protein (called E-FABP) has been described as binding to epidermal fatty acids with a strong affinity for fatty acids containing 18 carbon atoms, such as stearic acid, oleic, linoleic and linolenic acid, but with a weak or non-existent affinity for arachidonic acid and its derivatives (Siegenthaler, G. et al. (1994) Biochem. J. 302, 363–371). Therefore, this protein could play an important role in the transportation of certain fatty acids, but not in that of the arachidonic acid and its derivatives.

Furthermore, it is known that inflammatory illnesses, such as rheumatoid arthritis, cystic fibrosis, or skin disorders with an inflammatory component tied to the release of arachidonic acid or its derivatives, such a psoriasis, eczema, atopic dermatitis, or yet the healing of skin lesions, present a deregulation or a modification of the metabolism of fatty acids and more specifically of the arachidonic acid.

In the cosmetic field, we may think that a deregulation or modification of the metabolism of fatty acids is what causes dry skin or, on the contrary, oily skin, or yet a fragilization of the skin.

From this point of view, we sought to understand the capture, release and transportation mechanism of fatty acids by the skin cells, such as keratinocytes.

SUMMARY OF THE INVENTION

In this way, surprisingly so, we were able to identify and isolate, in particular from human keratinocytes, a heteromer that binds to fatty acids, and more specifically to arachidonic acid and/or oleic acid.

DETAILED DESCRIPTION OF THE INVENTION

Thus, the object of this invention is an isolated heteromer that binds arachidonic acid. More specifically, it also binds oleic acid.

This heteromer also binds another essential fatty acid, linoleic acid.

Because of this property, we can see the advantage of this heteromer in particular in the understanding of the capture, release or transportation mechanism of the arachidonic acid or its derivatives and/or in the identification of substances that are susceptible of modifying this transportation mechanism and therefore the biological activity resulting from the arachidonic acid. By derivatives of the arachidonic acid, we mean all biological derivatives of the arachidonic acid such as in particular, the hydroxyacids, the thromboxanes, the leukotrienes and the prostaglandins.

Therefore, another object of this invention is the use of this heteromer as a diagnostic tool, more specifically for inflammatory diseases or skin disorders with an inflammatory component linked to the release of the arachidonic acid or its derivatives (see above) In the same way, the heteromer allows for the evaluation of the biological activity of substances that are likely to be active in the treatment of inflammatory diseases or skin disorders with an inflammatory component linked to the release of the arachidonic acid or its derivatives (see above).

Indeed, thanks to the purification procedure of the heteromer that will be described later, we are aware that a skin with psoriasis contains approximately ten times more of this heteromer than a normal skin (whose purified quantity reaches approximately 4 pmol/mg of protein), The quantity of the heteromer found, in particular by the process of purification described later, is therefore one way of diagnosing a skin disorder, such as psoriasis.

From this discovery, we can also consider measuring the evolution of the quantity of isolated heteromer using the keratinocytes of a human being who is being treated with a substance that is likely to treat his inflammatory illness or skin disorder.

Preferably, this isolated heteromer shows a dissociation constant Kd that is less than or equal to 300 nM in relation to the arachidonic acid, and preferably less than or equal to 200 nM.

These dissociation constants are obtained by carrying out measurements using the carbon-dextran technique. This technique is as follows: aliquot portions of 0.5 μg of heteromer in solution in 100 μl of Tris buffer (50 mM Tris/HCl, 25 mM NaCl, 2.5 mM EDTA, 1 mM DTT at pH 7.5) containing 0.5% of gelatin and 1% of DMSO are incubated for 1 hour at 37° C. in the presence of increasing quantities of radiolabelled ligand, i.e, 0–10 μM for the oleic acid and the arachidonic acid. Then, each aliquot portion is treated with 50 μl a mixture of carbon-dextran T40® (5% and 0.05% respectively) at 0° C. for 10 minutes, then centrifuged at 10000 g and the radioactivity of the supernatant is measured. A saturation curve is established, and the Kd is calculated using the Scatchard plot.

In other respects, this heteromer shows a dissociation constant in relation to the oleic acid that is less than that of the E-FABP in relation to the same ligand, the E-FABP being the protein described in the Siegenthaler, G. et al. (1994) Biochem. J. 302, 363–371 publication.

More specifically, the heteromer consistent with the invention is a protein, and this protein has a molecular weight of approximately 34 kDa±10% (analysis in non denaturing conditions (filtration over gel)).

In general, the molecular weights have been determined by column filtration chromatography [(Superose 12) coupled with an HPLC]. The column, balanced with a 50 mM Tris/HCl buffer containing 0.2M of NaCl is graduated with protein standards of molecular weight ranging from 6.5 kDa to 150 kDa, then, an aliquot portion of heteromer is passed through the column to determine its molecular weight. The elution profile of the proteins is analyzed by the measurement of optical density (OD) at 280 nm.

This heteromer may also bind in quantity up to 1.5 times more arachidonic acid than oleic acid.

Indeed, when a determined quantity of heteromer in solution is incubated in the presence of 600 nM of radiolabelled arachidonic acid, then analyzed through a filtration column over gel [(Superose 12) balanced with a Tris/HCl buffer containing 0.2M NaCl and connected to a HPLC], the radioactive peak that co-elutes elutes at 34 kDa and corresponds to the radiolabelled arachidonic acid-heteromer complex is 1.5 times greater than if the experiment were performed in the same conditions, but with 600 nM of radiolabelled oleic acid.

Quite surprisingly, in conditions that are denaturing for the proteins (SDS-PAGE method), the analysis discloses that this isolated heteromer corresponds to a non-covalent complex of various sub-units, consisting of one protein called MRP8 which corresponds to the nucleotide and amino acid sequences of SEQ ID NOs: 1–2 and another protein called MRP14 which corresponds to the nucleotide and amino acid sequences of SEQ ID NOs: 3–4. More particularly, this heteromer consists of two MRP8 sub-units and one MRP14 sub-unit. These two proteins, MRP8 and MRP14, are in particular described in the Odink et al., (1987) Nature 330, 80–82 publication.

The purification process of the heteromer matches conventional steps of protein extraction from biological tissues, more specifically from skin tissues, such as in particular the keratinocytes of the skin.

The purification process of the heteromer that is implemented consists specifically of the following steps: approximately 5 g of psoriasis scales are homogenized in 15 ml of Tris/HCl buffer using a homogenizer (Polytron) then, the mixture is centrifuged at 100000 g for 1 hour at 4° C. The pellet is collected and suspended in 5 ml of the same buffer and centrifuged at 10000 g. The supernatant is eliminated. This washing operation is carried out two more times. Then, the pellet is treated in 15 ml of KCl buffer (10 mM Tris/CHl, 0.8M KCl, 10 mM monothioglycerol, 10% glycerol, 1 mM PMSF, 10 U/ml aprotinin, 10 mg/ml leupeptin) at a pH of 7.4 for 90 minutes at 4° C. This treatment is repeated once more. The supernatants are brought together and dialyzed overnight through a 20 mM imidazole buffer with a pH of 6, concentrated using a filtration cell with a dialysis membrane whose pore size is 3500 Da, the solution is then charged through a cation ion exchange column (Resource S). The elution is performed by a gradient consisting of the dialysis buffer but containing 0.5M of NaCl. The column is first standardized with an incubated sample with tritiated oleic acid.

The fractions that co-elute with the radioactive peak are gathered, dialyzed through a 20 mM Tris/HCl buffer, pH of 8.0 and the solution is concentrated. This solution is passed through a cation ion exchange column (Resource Q) balanced with the last buffer. The elution in the form of a gradient is performed with this Tris buffer containing 0.5M of NaCl. In the same way as above, the column has been standardized and only the proteins that co-elute with the radioactive peak are gathered, dialyzed through a 100 mM sodium phosphate buffer with a pH of 7.0 and concentrated The last purification step is carried out on a filtration column (Superose 12) balanced with the phosphate buffer. The protein peak that elutes at 34 kDa corresponds to the purified heteromer.

Preferably, the keratinocytes are human differentiated keratinocytes and more advantageously the keratinocytes come from psoriasis scales or from the infundibulum (epidermic invagination) of the fair follicle.

This heteromer can also be isolated from human leukocytes. Thus, this heteromer is also present in the macrophages of the dermis of the skin located around the epidermic peaks, these peaks are characteristic of inflammatory diseases of the skin, such as psoriasis.

Therefore, this invention relates in particular to a cosmetic or pharmaceutical composition, characterized by the fact that it contains, in an acceptable cosmetic or dermatologic environment, the heteromer described above. In particular, the object of the cosmetic composition is to improve the cosmetic aspect of the skin, in particular, by improving the barrier function of the epidermis.

The composition, when pharmaceutical, is preferably dermatologic.

It also relates to the use of this heteromer as medication, in particular for the preventive or curative treatment of hair loss or further for the acceleration of the healing process. Indeed, without involving any kind of theory, during the healing process, we notice a cell proliferation and differentiation that are greater than normal (uninjured skin), and this process accompanies an increase of the quantity of the heteromer consistent with the invention, it therefore seems that this heteromer is involved in the healing process.

Thus, the invention relates to the use of the heteromer as described above in a cosmetic composition or as medication, said heteromer or medication being conceived for the treatment of hair loss or for the acceleration of the healing process.

The quantity of the heteromer present in this composition may vary to a large extent, in particular in relation to the effect that is sought. In order to give an idea of values, the heteromer can be present at concentrations between $10^{-8}$ and 20% by weight in relation to the total weight of the composition.

The composition consistent with the invention can be administered by enteral, parenteral or topical pathways. Preferably, the topical pathway is used.

By topical pathway, we prefer the direct application on the skin, the scalp, the nails or the mucous membranes.

The composition consistent with the invention can be in all galenic forms. These compositions are prepared according to the usual methods.

A cosmetically or dermatologically acceptable environment generally corresponds to an environment that is compatible with the skin, the scalp, the nails or the mucous membranes. The composition that contains the heteromer can therefore be applied to the face, the neck, the hair or the nails, or any other cutaneous area of the body (axillary, sub-mammary areas, the folds of the elbow, etc.)

By topical pathway, the compositions consistent with the invention come, in particular, in the form of hydroalcoholic, water or oil substances, of dispersions that are of the lotion or serum type, of anhydrous or lipophilic gels, of emulsions of liquid or semi-liquid consistency of the milk type obtained by the dispersion of a fatty phase in an aqueous phase (H/E) or inversely (E/H), or in the form of mixtures or emulsions of soft, semi-solid or solid consistency of the cream or gel type, or further of microemulsions, microcapsules, microparticles or vesicular dispersions of the ionic and/or non ionic type. These compositions are prepared according to the usual methods By enteral pathway, the compositions consistent with the invention can be in the form of tablets, capsules, sugar-coated pills, syrups, suspensions, solutions, powders, pellets, emulsions, microspheres or nanospheres, or lipidic or polymeric vesicles allowing for a controlled release.

By parenteral pathway, the compositions can be in the form of solutions or suspensions for perfusion or for injection.

They can also be used for the scalp in the form of aqueous, alcoholic or hydroalcoholic solutions, or in the form of creams, gels, emulsions, foams, or further in the form of compositions for aerosol use also containing a propellant under pressure.

The quantities of the various components of the compositions consistent with the invention are those used conventionally in the fields in question.

These compositions consist in particular of shaving foams, cleansing, protective, treatment or care creams for the face, the hands, the feet and for the large anatomic wrinkles or for the body (for example day creams, night creams, cleansing creams, foundation creams, sunscreen creams), fluid foundations, cleansing milks, body barrier or treatment milks, sun-screen milks or better yet, after-sun milks, lotions, gels or foams for skin care, such as lotions for cleansing or disinfecting, sunscreen lotions, self-tanning lotions, compositions for the bath, deodorizing compositions containing a bactericidal agent, after-shave gels or lotions, depilatory creams, compositions against insect bites, compositions against pain or compositions for the treatment of certain skin disorders such as those mentioned previously, The compositions according to the invention can also consist of solid preparations that make soaps or cleansing cakes.

The compositions can also be conditioned in the form of compositions for aerosol use also containing a propellant under pressure, The heteromer can also be incorporated in various compositions for hair care or treatment, and in particular in shampoos, possibly antiparasitic, in lotions for permanents, treatment lotions, hair gels or creams, hair coloring compositions (in particular oxidation coloring) possibly in the form of coloring shampoos, hair conditioning lotions, permanent compositions (in particular compositions for the first step of a permanent), hair loss gels or lotions, etc.

The compositions of the invention can also have a bucco-dental use, for example a toothpaste or mouth wash. In this case, the compositions can contain the usual adjuvants or ancillaries for compositions that have a buccal use and in particular surfactants, thickening agents, humectants, polishing agents such as silica, various active ingredients such as fluorides, in particular sodium fluoride, and possibly sweetening agents such as sodium saccharinate.

When the invention's composition is an emulsion, the proportion of the fatty phase can reach from 5% to 80% by weight, and preferably from 5% to 50% by weight in relation to the total weight of the composition, The oils, emulsifiers and co-emulsifiers used in the composition in the form of emulsion are chosen among those conventionally used in the cosmetic and pharmaceutical fields. The emulsifier and the co-emulsifier are present in the composition in a proportion ranging from 0.3% to 30% by weight, and preferably from 0.5% to 30% or even better from 0.5% to 20% by weight in relation to the total weight of the composition, In addition, the emulsion can contain lipidic vesicles.

When the composition of the invention is a solution or an oil gel, the fatty phase can represent more than 90% of the total weight of the composition.

As it is known, the composition of the invention can also contain the usual adjuvants used in the cosmetic or pharmaceutical fields, such as hydrophilic or lipophilic gelatinizers, hydrophilic or lipophilic actives, preservatives, antioxidants, solvents, perfumes, fillers, filters, bactericides, odor absorbers and dyes. The quantities of these different adjuvants are those used conventionally in the cosmetic and pharmaceutical fields, and range for example from 0.01% to 10% of the total weight of the composition. These adjuvants, depending on their nature, can be introduced in the fatty phase, in the aqueous phase and/or in the lipidic spherical particles.

As far as oils that can be used in the invention are concerned, we can name the mineral oils (liquid paraffin), vegetable oils (liquid fraction of karite butter, sunflower oil), animal oils (perhydrosqualene), synthesis oils (Purcellin oil), siliconized oils (cyclomethicone) and fluorinated oils (perfluoropolyethers). One can also use cetyl alcohol, fatty acids (stearic acid), waxes (paraffin, caranda, bees wax) as fats.

As far as emulsifiers that can be used in the invention are concerned, we can name for example glycerol stearate, polysorbate 60 and the PEG-6/PEG-32/Glycol Stearate mixture sold under the name Tefose$^R$63 by the Gattefosse company.

As far as solvents that can be used in the invention are concerned, we can name the low alcohols, in particular ethanol and isopropanol, propylene glycol.

As far as hydrophilic gelatinizers are concerned, we can name the carboxyvinyl polymers (carbomer), the acrylic copolymers such as the acrylate/alkylacrylate copolymers, the polyacrylamides, the polysaccharides such as the hydroxypropylcellulose, natural gum and clay, and, as lipophilic gelatinizers, we can name the modified clays such as Bentone, the fatty acid metal salts such as aluminum stearates and hydrophobic silica or yet the ethyl cellulose, polyethylene.

As hydrophilic actives, we can use protein or protein hydrolyzates, amino acids, polyols, urea, allantoin, sugars and sugar derivatives, water soluble vitamins, starch and vegetable extracts, in particular those from aloe vera.

As lipophilic actives, we can use retinol (vitamin A) and its derivatives, tocopherol (vitamin E) and its derivatives, ceramides, essential oils.

In the following or preceding text, the percentages given are expressed in weight, except where otherwise indicated, EDTA means ethylenediaminetetraacetic acid, DTT means dithiothreitol, DMSO means dimethylsulfoxide and PMSF means methanesulfonyl phenyl fluoride.

EXAMPLE

Heteromer Measuring Method

This method allows for the measuring of the quantity of the heteromer according to the invention in biological samples, excluding any form of contamination by the monomers of which it consists, MRP8 and MRP14, or by their non functional complexes (that do not migrate). The technique consists in separating the proteins that are extracted from a biological environment, such as in particular the tissue extracts, cytosolic, membrane extracts, synovial and cephalorhachidian liquids on a polyacrylamide gel (PAGE) in acid condition such as at a pH of 4.3. During the electrophoresis, the polarity of the electrodes is reversed so that the positively charged proteins at this pH migrate in this gel. Thus, the conventional polyacrylamide gels (pH 8.8, migration towards the anode) can be analyzed by this method.

Solutions for the preparation of the acid gel

A: solution for the pH 4.3 migration gel
24 ml of KOH 1 M
2 ml of N,N,N',N'-tetramethylethylenediamine (TEMED)
8 ml of acetic acid
qs at 50 ml of water
B. solution for the a pH 5.8 concentration gel
24 ml of KOH 1 M
0.23 ml of TEMED
1.44 ml of acetic acid
qs at 50 ml of water
C: acrylamide solution for the migration gel
6.65 g of acrylamide
0.1 g of N,N'-methylene-bis-acrylamide
qs at 50 ml of water
D: acrylamide solution for the concentration gel
2.5 g of acrylamide
0.625 g of N,N'-methylene-bis-acrylamide
qs at 50 ml of water
E. buffer solution for the sample
0.05% fuchsine red, 75% glycerol
F: buffer solution for the pH 4.5 4× migration
31.2 g of β-alanine
8 ml of acetic acid
qs at 1 l of water Preparation of the Migration Gel Between the two glass plates of the apparatus (BioRad mini-gels), we pour 3.5 ml per gel of the mixture consisting of: 1 ml of solution A+4.5 ml of solution C+1.5 ml of H20+1 ml of ammonium peroxydisulfate (APS) (56 mg/5 ml). It is left to cure.

Preparation of the Concentration Gel

When the migration gel is cured, we pour the following mixture over it: 1 ml of solution B+4 ml of solution D+2.25 ml of H20+0.75 ml of APS. We add the comb and let it cure for a long time.

The protein samples are prepared in the E sample buffer (containing 5 µg per sample of cytochrome C in order to improve the quality of the migration) and are then deposited in the wells, The protein samples can also be incubated with a radiolabelled ligand of the heteromer consistent with the invention such as tritiated oleic acid.

The F buffer of the tanks is diluted 4 times with distilled water and the apparatus is switched on at 200V for 45 minutes.

This method of acid gel is inspired from Reisfald R A, Lewis U J, Willian D E, Nature 195:281–283, 1962.

Detection and Measuring of the Heteromer (a) The isolation of the heteromer can be performed directly on the gel by coloring it with a coomassie blue. The blue band that appears above that of the cytochrome C corresponds to that of the heteromer consistent with the invention.

(b) By immunodetection on gel, it is possible to obtain great sensitivity The gel proteins are then electro-transferred on a cellulose nitrate or polyvinylpyrrolidone sheeting in a 30 mM sodium phosphate buffer with a pH of 6.4 under a constant 20V for 1 hour. The membrane is then incubated in an isotonic phosphate (PBS) buffer containing 0.5% of powered skim milk, 0.2% of Tween 20 (polysorbate).

The monoclonal antibodies directed against MRP8 and MRP14 (Biomedicals, Switzerland) are used in a 1/50 dilution. The polyclonal antibodies directed against the heteromer of this invention originating from the rabbit are used in a 1/500 dilution. Thus, all these antibodies, used separately or together, bind to the heteromer according to the invention. The immunoreactive band of the heteromer in accordance with the invention is visualized by using antibodies directed against the antibodies listed above originating from goats that are complexed to the peroxidase and put in the presence of the substrates, 3.3'-diaminobenzidine and H2O2.

The comparative analysis of the different wells is performed using densitometry. It can also be performed by direct autoradiography when the sample has been incubated with a radiolabelled ligand.

These three methods have been performed (coomassie blue, antibodies and tritiated oleic acid) using: psoriasis scales, a cytosolic fraction of psoriasis scales, a membrane extract of psoriasis scales, a cytosolic fraction of normal human neutrophils and a membrane fraction of normal human neutrophils.

We notice that the band with the strongest electrophoretic mobility corresponds to the heteromer in accordance with the invention.

This analysis also reveals that the quantity of the heteromer according to the invention is stronger in the membrane extract of psoriasis scales than in that of the cytosolic fraction of psoriasis scales, the opposite is observed for the normal human neutrophils.

What is claimed is:

1. A purified isolated protein which specifically binds arachidonic acid, said protein being a heteromer which is a non-covalent complex of two migration inhibitory factor related protein 8 (MRP8) subunits and one migration inhibitory factor related protein 14 (MRP14) subunit and which has a molecular weight of 34 kDa±10%.

2. The protein of claim 1, which has a Kd dissociation constant which is less than or equal to 300 nM in relation to arachidonic acid.

3. The protein of claim 2, wherein said Kd dissociation constant is less than or equal to 200 nM in relation to arachidonic acid.

4. A pharmaceutical, dermatological or cosmetic composition which comprises a pharmaceutically, dermatologically, or cosmetically effective amount of the protein of claim 3, and a pharmaceutically, dermatologically or cosmetically acceptable carrier.

5. A pharmaceutical, dermatological or cosmetic composition which comprises a pharmaceutically, dermatologically, or cosmetically effective amount of the protein of claim 2, and a pharmaceutically, dermatologically or cosmetically acceptable carrier.

6. A purified protein which specifically binds linoleic acid, said protein being a heteromer which is a non-covalent complex of two migration inhibitory factor related protein 8 (MRP8) subunits and one migration inhibitory factor related protein 14 (MRP14) subunit and which has a molecular weight of 34 kDa±10%.

7. A purified protein which specifically binds oleic acid, said protein being a heteromer which is a non-covalent complex of two migration inhibitory factor related protein 8 (MRP8) subunits and one migration inhibitory factor related protein 14 (MRP14) subunit and which has a molecular weight of 34 kDa±10%.

8. A pharmaceutical, dermatological or cosmetic composition which comprises a pharmaceutically, dermatologically, or cosmetically effective amount of the protein of claim 7, and a pharmaceutically, dermatologically or cosmetically acceptable carrier.

9. The protein of claim 1, which is isolated from human keratinocytes or human leucocytes.

10. The protein of claim 9, wherein said keratinocytes are isolated from psoriasis scales.

11. A pharmaceutical, dermatological or cosmetic composition which comprises a pharmaceutically, dermatologically, or cosmetically effective amount of the protein of claim 9, and a pharmaceutically, dermatologically or cosmetically acceptable carrier.

12. A pharmaceutical, dermatological or cosmetic composition which comprises a pharmaceutically, dermatologically, or cosmetically effective amount of the protein of claim 10, and a pharmaceutically, dermatologically or cosmetically acceptable carrier.

13. A pharmaceutical, dermatological or cosmetic composition which comprises a pharmaceutically, dermatologically, or cosmetically effective amount of the protein of claim 1, a pharmaceutically, dermatologically or cosmetically acceptable carrier.

14. A pharmaceutical, dermatological or cosmetic composition which comprises a pharmaceutically, dermatologically, or cosmetically effective amount of the protein of claim 1, and a pharmaceutically, dermatologically or cosmetically acceptable carrier.

15. The composition of claim 13, which is in a form selected from the group consisting of a cream, fluid, milk, lotion, emulsion, gel, solid, paste, and an aerosol.

16. The composition of claim 13, wherein the amount of said protein ranges from 10.6 to 20% by weight of the composition.

17. A dermatological composition which comprises a dermatologically, effective amount of the polypeptide of claim 1, and a dermatologically acceptable carrier.

18. A cosmetic composition which comprises a cosmetically effective amount of the polypeptide of claim 1, and a cosmetically acceptable carrier.

19. A pharmaceutical composition which comprises a pharmaceutically effective amount of the polypeptide of claim 1, and a dermatologically acceptable carrier.

* * * * *

SEQUENCE LISTING

<160> NUMBER OF SEQ ID NOS: 4

<210> SEQ ID NO 1
<211> LENGTH: 418
<212> TYPE: DNA
<213> ORGANISM: Artificial Sequence
<220> FEATURE:
<223> OTHER INFORMATION: Nucleotide and amino acid sequence of MRP-8.
<221> NAME/KEY: CDS
<222> LOCATION: (57)..(338)

<400> SEQUENCE: 1

```
atgtctcttg tcagctgtct ttcagaagac ctggtggggc aagttccgtg ggcatc atg     59
                                                               Met
                                                                 1 ttg acc gag ctg gag aaa gcc ttg aac tct atc atc gac gtc tac cac    107
Leu Thr Glu Leu Glu Lys Ala Leu Asn Ser Ile Ile Asp Val Tyr His
      5                  10                  15 aag tac tcc ctg ata aag ggg aat ttc cat gcc gtc tac agg gat gac    155
Lys Tyr Ser Leu Ile Lys Gly Asn Phe His Ala Val Tyr Arg Asp Asp
         20                  25                  30 ctg aag aaa ttg cta gag acc gag tgt cct cag tat atc agg aaa aag    203
Leu Lys Lys Leu Leu Glu Thr Glu Cys Pro Gln Tyr Ile Arg Lys Lys
     35                  40                  45 ggt gca gac gtc tgg ttc aaa gag ttg gat atc aac act gat ggt gca    251
Gly Ala Asp Val Trp Phe Lys Glu Leu Asp Ile Asn Thr Asp Gly Ala
 50                  55                  60                  65 gtt aac ttc cag gag ttc ctc att ctg gtg ata aag atg ggc gtg gca    299
Val Asn Phe Gln Glu Phe Leu Ile Leu Val Ile Lys Met Gly Val Ala
                 70                  75                  80 gcc cac aaa aaa agc cat gaa gaa agc cac aaa gag tag ctgagttact     348
Ala His Lys Lys Ser His Glu Glu Ser His Lys Glu
                 85                  90 gggcccagag gctgggcccc tggacatgta cctgcagaat aataaagtca tcaatacctc   408
aaaaaaaaaa                                                           418
```

<210> SEQ ID NO 2
<211> LENGTH: 93
<212> TYPE: PRT
<213> ORGANISM: Artificial Sequence
<220> FEATURE:
<223> OTHER INFORMATION: Amino acid sequence of MRP-8.

<400> SEQUENCE: 2

```
Met Leu Thr Glu Leu Glu Lys Ala Leu Asn Ser Ile Ile Asp Val Tyr
  1               5                  10                  15

His Lys Tyr Ser Leu Ile Lys Gly Asn Phe His Ala Val Tyr Arg Asp
                 20                  25                  30

Asp Leu Lys Lys Leu Leu Glu Thr Glu Cys Pro Gln Tyr Ile Arg Lys
             35                  40                  45

Lys Gly Ala Asp Val Trp Phe Lys Glu Leu Asp Ile Asn Thr Asp Gly
         50                  55                  60

Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90
```

<210> SEQ ID NO 3
<211> LENGTH: 462
<212> TYPE: DNA
<213> ORGANISM: Artificial Sequence
<220> FEATURE:
<223> OTHER INFORMATION: Nucleotide and amino acid sequence of MRP-14.
<221> NAME/KEY: CDS
<222> LOCATION: (45)..(389)

<400> SEQUENCE: 3

```
aaaacactct gtgtggctcc tcggctttga cagagtgcaa gacg atg act tgc aaa      56
                                                Met Thr Cys Lys
                                                1 atg tcg cag ctg gaa cgc aac ata gag acc atc atc aac acc ttc cac     104
Met Ser Gln Leu Glu Arg Asn Ile Glu Thr Ile Ile Asn Thr Phe His
5                   10                  15                  20 caa tac tct gtg aag ctg ggg cac cca gac acc ctg aac cag ggg gaa     152
Gln Tyr Ser Val Lys Leu Gly His Pro Asp Thr Leu Asn Gln Gly Glu
                25                  30                  35 ttc aaa gag ctg gtg cga aaa gat ctg caa aat ttt ctc aag aag gag     200
Phe Lys Glu Leu Val Arg Lys Asp Leu Gln Asn Phe Leu Lys Lys Glu
            40                  45                  50 aat aag aat gaa aag gtc ata gaa cac atc atg gag gac ctg gac aca     248
Asn Lys Asn Glu Lys Val Ile Glu His Ile Met Glu Asp Leu Asp Thr
        55                  60                  65 aat gca gac aag cag ctg agc ttc gag gag ttc atc atg ctg atg gcg     296
Asn Ala Asp Lys Gln Leu Ser Phe Glu Glu Phe Ile Met Leu Met Ala
    70                  75                  80 agg cta acc tgg gcc tcc cac gag aag atg cac gag ggt gac gag ggc     344
Arg Leu Thr Trp Ala Ser His Glu Lys Met His Glu Gly Asp Glu Gly
85                  90                  95                  100 cct ggc cac cac cat aag cca ggc ctc ggg gag ggc acc ccc taa         389
Pro Gly His His His Lys Pro Gly Leu Gly Glu Gly Thr Pro
                105                 110 gaccacagtg gccaagatca cagtggccac ggccacggcc acagtcatgg tggccacggc    449
cacagccacc cat                                                       462

<210> SEQ ID NO 4
<211> LENGTH: 114
<212> TYPE: PRT
<213> ORGANISM: Artificial Sequence
<220> FEATURE:
<223> OTHER INFORMATION: Amino acid sequence of MRP-14.

<400> SEQUENCE: 4

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
        50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```